US00PP12454P2

(12) United States Plant Patent
Utecht

(10) Patent No.: US PP12,454 P2
(45) Date of Patent: Mar. 12, 2002

(54) GERANIUM PLANT NAMED 'FISSALM'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/773,006

(22) Filed: Jan. 31, 2001

(51) Int. Cl.[7] ..... A01H 5/00
(52) U.S. Cl. ..... Plt./328
(58) Field of Search ..... Plt./327, 328

(56) References Cited

PUBLICATIONS

GTITM UPOVROM Citation for 'Fissalm' as per QZ PBR 991046; Jul. 20, 1999.*
Official Gazette of the Community Plant Variety Office Oct. 15, 1999; European Union Application, denomination, decision for 'FISSALM'.

German Application for 'FISSALM' Sep. 15, 1998.

German Proposed Denomination for 'FISSALM' Aug. 15, 1999.

Plant Varieties Journal, Jan. 2001, No. 38, pp. 48–49 (Canada).

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fissalm', as described and illustrated, and particularly characterized by the combined features of salmon-pink semi-double flowers, large umbels, borne high above the foliage, relatively large, intense green foliage with strong zonation, and medium to tall, fairly round plant habit.

1 Drawing Sheet

BACKGROUND OF THE INVENTION

The present invention comprises a new and distinct cultivar of geranium, botanically known as *Pelargonium zonale*, and hereinafter referred to by the cultivar name 'Fissalm'.

'Fissalm' is a product of a planned breeding program which had the objective of creating new geranium varieties with intense salmon flower color, in combination with medium-green foliage, and well-branched plant habit.

'Fissalm' originated from a hybridization made by the inventor Angelika Utecht in a controlled breeding program in Galdar, Gran Canaria, Spain, in 1992.

The female parent was a hybrid seedling, no. 1943a (unpatented), having intense salmon, semi-double flowers and medium-green foliage with strong zonation. The male parent of 'Fissalm' was the hybrid seedling no. 1216-3 (unpatented), characterized by uniform salmon colored, single-type flowers, light to medium-green foliage with strong zonation, and vigorous growth.

'Fissalm' was selected as one flowering plant within the progeny of the stated cross by Angelika Utecht in 1993 in a controlled environment in Galdar, Gran Canaria, Spain.

The first act of asexual reproduction of 'Fissalm' was accomplished when vegetative cuttings were taken from the initial selection in the fall of 1993 in a controlled environment in Galdar, Gran Canaria, Spain, by, or under the supervision of, Angelika Utecht. Horticultural examination of plants grown from cuttings of the plant initiated in May 1995 in Hillscheid, Federal Republic of Germany, and continuing thereafter, has demonstrated that the combination of characteristics as herein disclosed for 'Fissalm' are firmly fixed and are retained through successive generations of asexual reproduction.

'Fissalm' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fissalm' in combination distinguish this geranium as a new and distinct cultivar:

1. Salmon-pink, semi-double flowers;

2. Large, round flowers, and wide, somewhat flattened semi-spherically shaped umbel;

3. Medium-green, relatively large leaves with strong zonation;

4. Moderately vigorous growth, and medium to tall, bushy plant habit; and

5. Early to medium spring flowering response.

Of the many commercial cultivars known to the present inventor, the most similar in compariosn to 'Fissalm' is the variety 'Fisorange', U.S. Plant Pat. Ser. No. 09/632,245.

In comparison to 'Fisorange', 'Fissalm' has a slightly more pink, less orange general flower color, lighter margins of petals, larger flowers and umbels, wider leaves, and somewhat taller plant habit.

In comparison to the female seed parent, 'Fissalm' has larger umbels, more vigorous growth habit, and fewer inner petals.

BRIEF DESCRIPTION OF THE DRAWING

The accompanying photographic drawing shows typical flower and foliage characteristics of 'Fissalm' with colors being as true as possible with an illustration of this type. The photograph shows a flowering potted plant. The measurements were taken in Langley, British Columbia, Canada on Jul. 20, 2000, 15 weeks after planting of rooted cuttings into 6 inch pots. The plants had not been pinched.

In the following description color references are made to The Royal Horticultural Society Colour Chart (R.H.S.). The color values were determined indoors from plants developed in a green-house in May, 2000 in Hillscheid, Germany.

Classification:

*Botanical.*—A hybrid of the species *Pelargonium zonale*. L'Hérit.

*Commercial.*—Zonal geranium, cv. 'Fissalm'.

Inflorescence:

*Umbel.*—Shape: Somewhat flattened semi-sphere. Average diameter: 119 mm. Average depth: 60 mm. Peduncle length: 165 mm. Peduncle color: mainly light green, RHS 143 A, weak infusion of anthocyanin, brownish, RHS 179 B, may occur. Pedicel length: 28 mm. Pedicel color: Base light green, RHS 143 C, middle RHS 179 B, tip RHS 179 A. Number of flowers per umbel: about 30–40. Lastingness of the umbel: Approximately 16–18 days at 18° C.

*Corolla.*—Average diameter: 45 mm. Form: Semi-double. Shape: Round, slightly cup-shaped. Number of petals: 8–10. Size of petals: Upper petals are 23–25 mm long, 17–19 mm wide, lower petals are 21–23 mm long, 19–21 mm wide. Shape of petals: Obovate, attenuate base, upper end weakly rounded, margin entire. Color (general tonality from a distance of three meters): salmon-pink with slightly lighter margin. Color of upper petals: RHS 40 B, margin: from RHS 43 C to RHS 43 D, lower surface: orange, RHS 41 B. Markings of upper petals: absent or very weak veins, slightly darker than the main flower color. Color of lower petals: RHS 40 B, margin from RHS 43 C to RHS 43 D, lower surface: RHS 43 D, lightening toward the base of the petals, RHS 49 B, no markings. Number of petaloids: 1–3. Color of petaloids: Upper surface RHS 40 B, lower surface RHS 43 D. Color of sepals: Outer surface light green, RHS 143 C, weak reddish-brown coloring near the base, RHS 179 B, inner surface light green, RHS 143 C, base weak reddish brown, RHS 179 B. Number of sepals: 5. Size of sepals: 10–11 mm in length, 4–5 mm in diameter for the largest upper sepal, 2–3 mm in diameter for the other sepals. Shape of sepals: Linear to lanceolate, acute tip, truncate base, surface with weak, short pubescence, margin entire.

*Bud (just prior to petals unfolding).*—Shape: Elliptical. Sepal Color (lower part): Light green, RHS 143 C, slightly reddish at the base, near RHS 179 B. Petal Color (upper part): Salmon to white, marbled, from RHS 43 C to RHS 49 B. Length: 15 mm. Width: 9 mm.

*Reproductive organs.*—Androecium: 5–7 fertile anthers, whitish filaments, orange pollen, RHS 33 A, plentiful pollen production. Gynoecium: 5–6 lobed, salmon-orange stigma, whitish style, one pistil per flower. Fertility/seed set: Occasionally a few seeds are developed, oblong shape, 4–5 mm, brown, RHS 177 B.

*Spring flow. response period.*—In Hillscheid, Germany, 2000, plants had on average 1.5 flowers opened 8 weeks after planting of rooted cuttings.

*Outdoor flower production.*—Medium number of flowers, the flower count in 2000 in Hillscheid, Germany, indicated about 3–3.5 inflorescences per plant in mid May.

*Durability.*—Good stability of flower color, little fading toward dull pink, RHS 48 B, when maturing or wilting, relatively good rain resistance.

*Lastingness of the individual bloom.*—Approximately 8 days at 18° C.

*Fragrance.*—None.

Plant:

*Foliage.*—Form: Kidney-shaped, weakly rounded, very weak lobes. Base: Cordate with open gap between the lower ends of leaf. Margin: Bicrenated. Texture: Slightly velvety. Size of leaf: 89 mm wide, 50–55 mm long. Color of upper surface: Intense green, approximately RHS 137 B. Color of lower surface: RHS 137 D. Color of zonation: Relatively strong, brown, about RHS 166 A. Petiole size: 45–55 mm in length, 3 mm in diameter. Petiole color: RHS 143 A.

*General appearance and form.*—Stem color: Green, RHS 143 A. Internode length: 20–25 mm. Branching pattern: 6.4 branches. Plant size: 26 cm in height, as measured from the soil to the surface of the foliage canopy, without the inflorescences; 35 cm wide.

*Disease/pest resistance/susceptibility.*—No observations to date.

I claim:

1. A new and distinct cultivar of geranium plant named 'Fissalm', as described and illustrated.

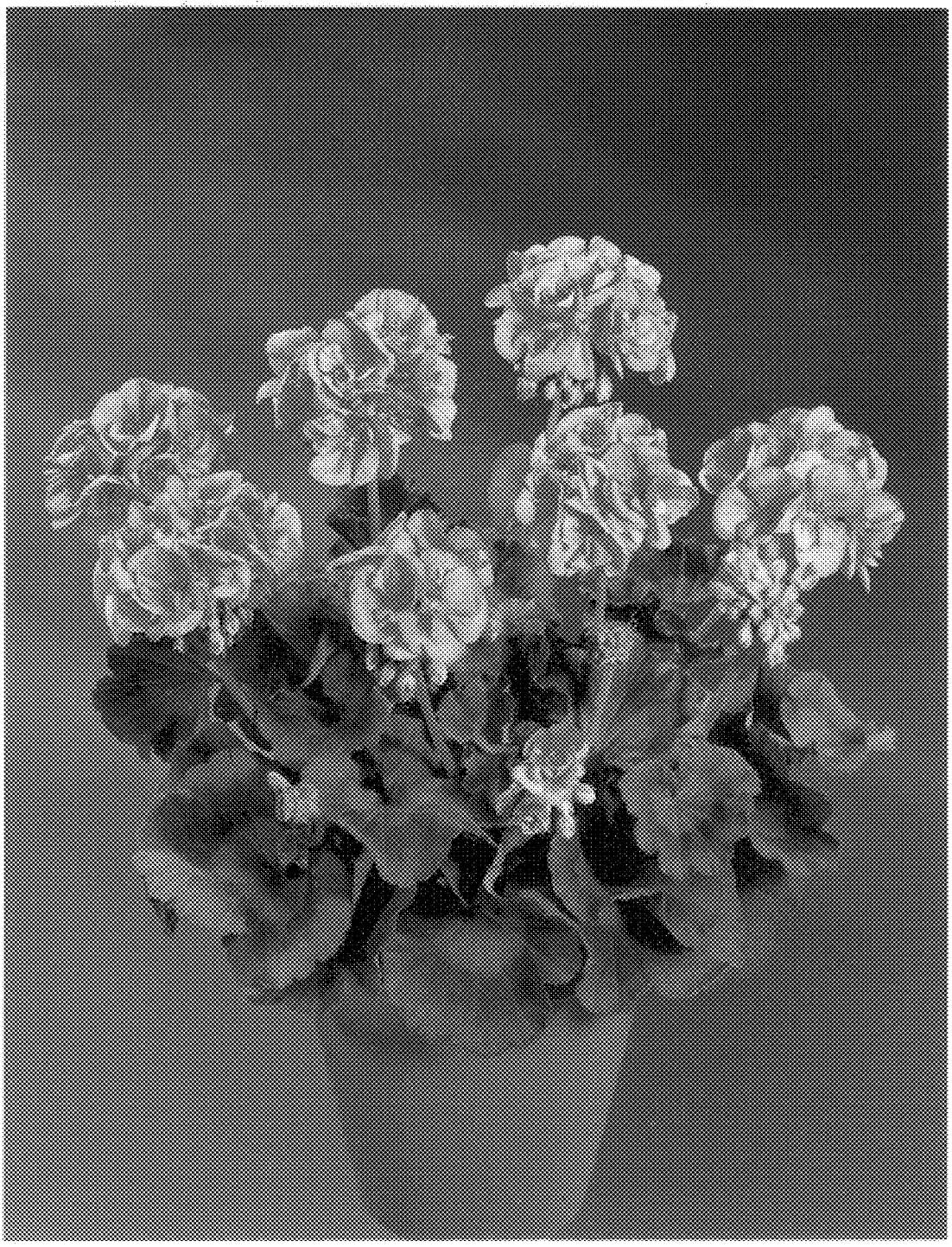

* * * * *